US011045423B2

(12) United States Patent
Bandi et al.

(10) Patent No.: US 11,045,423 B2
(45) Date of Patent: Jun. 29, 2021

(54) ANTI-RETROVIRAL COMPOSITIONS

(71) Applicant: HETERO LABS LIMITED, Telangana (IN)

(72) Inventors: Parthasaradhi Reddy Bandi, Telangana (IN); Khadgapathi Podile, Telangana (IN); Sunil Deviprasad Tiwari, Telangana (IN); Prakash Shetiya, Telangana (IN); Balakrishnaiah Medum, Telangana (IN)

(73) Assignee: HETERO LABS LIMITED, Telangana (IN)

( * ) Notice: Subject to any disclaimer, the term of this patent is extended or adjusted under 35 U.S.C. 154(b) by 182 days.

(21) Appl. No.: 16/324,231

(22) PCT Filed: Jul. 27, 2017

(86) PCT No.: PCT/IB2017/054571
§ 371 (c)(1),
(2) Date: Feb. 8, 2019

(87) PCT Pub. No.: WO2018/029561
PCT Pub. Date: Feb. 15, 2018

(65) Prior Publication Data
US 2019/0175508 A1   Jun. 13, 2019

(30) Foreign Application Priority Data
Aug. 8, 2016  (IN) .............................. 201641026997

(51) Int. Cl.
*A61K 9/24* (2006.01)
*A61P 31/18* (2006.01)
*A61K 9/20* (2006.01)
*A61K 31/635* (2006.01)
*A61K 31/5365* (2006.01)
*A61K 31/427* (2006.01)
*A61K 45/06* (2006.01)
*A61J 3/10* (2006.01)
*A61K 9/48* (2006.01)
*A61K 31/34* (2006.01)
*A61K 31/5383* (2006.01)

(52) U.S. Cl.
CPC ............... *A61K 9/209* (2013.01); *A61J 3/10* (2013.01); *A61K 9/2072* (2013.01); *A61K 9/2077* (2013.01); *A61K 9/2095* (2013.01); *A61K 9/48* (2013.01); *A61K 31/34* (2013.01); *A61K 31/427* (2013.01); *A61K 31/5365* (2013.01); *A61K 31/5383* (2013.01); *A61K 31/635* (2013.01); *A61K 45/06* (2013.01); *A61P 31/18* (2018.01)

(58) Field of Classification Search
None
See application file for complete search history.

(56) References Cited

U.S. PATENT DOCUMENTS

| | | | | |
|---|---|---|---|---|
| 4,591,500 A | * | 5/1986 | Scapinelli | A61J 3/10 424/401 |
| 4,851,230 A | * | 7/1989 | Tencza | A61J 3/10 424/467 |
| 5,541,206 A | | 7/1996 | Kempf et al. | |
| 5,843,946 A | | 12/1998 | Vazquez et al. | |
| 6,126,767 A | * | 10/2000 | Smith | A61J 3/005 156/308.8 |
| 7,700,645 B2 | | 4/2010 | Vermeersch et al. | |
| 8,129,385 B2 | | 3/2012 | Johns et al. | |
| 8,148,374 B2 | | 4/2012 | Desai et al. | |
| 9,339,470 B2 | * | 5/2016 | Lulla | A61K 9/209 |
| 2007/0071822 A1 | | 3/2007 | Dansereau et al. | |
| 2010/0189783 A1 | | 7/2010 | Smans et al. | |
| 2011/0008429 A1 | * | 1/2011 | Lulla | A61K 9/209 424/465 |
| 2014/0037724 A1 | | 2/2014 | Dahl et al. | |
| 2014/0142070 A1 | | 5/2014 | Dalaet et al. | |
| 2015/0272888 A1 | | 10/2015 | Rahmouni et al. | |
| 2016/0008374 A1 | | 1/2016 | Geleziunas et al. | |
| 2016/0038502 A1 | | 2/2016 | Koo et al. | |
| 2016/0081985 A1 | | 3/2016 | Menning et al. | |
| 2019/0175509 A1 | | 6/2019 | Bandi et al. | |
| 2019/0175511 A1 | | 6/2019 | Bandi et al. | |

FOREIGN PATENT DOCUMENTS

| | | | |
|---|---|---|---|
| WO | 2009013356 A2 | 1/2009 | |
| WO | 2009135179 A2 | 11/2009 | |
| WO | 2013004818 A1 | 1/2013 | |
| WO | 2014125124 A1 | 8/2014 | |
| WO | 2014184553 A1 | 11/2014 | |
| WO | WO-2014184553 A1 * | 11/2014 | ........... A61K 31/675 |

(Continued)

OTHER PUBLICATIONS

Prescribing Information: TIVICAY (dolutegravir) tablets. ViiV Healthcare (Aug. 2015).*
International Search Report and Written Opinion; International Application No. PCT/IB17/54571; International Filing Date Jul. 27, 2017; dated Nov. 6, 2017; 8 pages.
Marzolini et al.; "Cobicistat Versus Ritonavir Boosting and Differences in the Drug-Drug Interaction Profiles With Co-Medications"; J Antimicrob Chemother; 71; pp. 1755-1758; (2016).

*Primary Examiner* — Bethany P Barham
*Assistant Examiner* — Peter Anthopolos
(74) *Attorney, Agent, or Firm* — Cantor Colburn LLP

(57) ABSTRACT

The present invention relates to pharmaceutical antiretroviral compositions comprising a combination of antiretroviral agents (darunavir, dolutegravir and ritonavir), the manufacturing process thereof and use of the said compositions for the prevention, treatment or prophylaxis of HIV infection.

9 Claims, No Drawings

(56) References Cited

FOREIGN PATENT DOCUMENTS

WO 2016016279 A1 2/2016

\* cited by examiner

ANTI-RETROVIRAL COMPOSITIONS

CROSS REFERENCE TO RELATED APPLICATIONS

This patent application is a § 371 of PCT/IB2017/054571, filed on Jul. 27, 2017, which claims priority to Indian patent application number IN 201641026997, filed on Aug. 8, 2016, under the provisions of 35 U.S.C. § 119 and the International Convention for the protection of Industrial Property, the contents of which are incorporated by reference herein in their entirety.

FIELD OF THE INVENTION

The present invention relates to pharmaceutical antiretroviral compositions comprising a combination of antiretroviral agents with the manufacturing process thereof and use of the said compositions for the prevention, treatment or prophylaxis of diseases caused by retro viruses, specifically acquired immune deficiency syndrome or an HIV infection.

BACKGROUND OF THE INVENTION

Acquired Immune Deficiency Syndrome (AIDS) causes a gradual breakdown of the body's immune system as well as progressive deterioration of the central and peripheral nervous systems. Since its initial recognition in the early 1980's, AIDS has spread rapidly and has now reached epidemic proportions within a relatively limited segment of the population. Intensive research has led to the discovery of the responsible agent, human T-lymphotropic retrovirus 111 (HTLV-111), now more commonly referred to as the human immunodeficiency viruses or HIV.

The treatment of HIV infection, known as cause of the acquired immunodeficiency syndrome (AIDS), remains a major medical challenge. HIV is able to evade immunological pressure, to adapt to a variety of cell types and growth conditions and to develop resistance against currently available drug therapies. Various available categories of drugs for treating HIV are nucleoside reverse transcriptase inhibitors (NRTIs), non-nucleoside reverse transcriptase inhibitors (NNRTIs), nucleotide reverse transcriptase inhibitors (NtRTIs), HIV-protease inhibitors, fusion inhibitors, CCR5 inhibitors and integrase inhibitors.

Although effective in suppressing HIV, each of these drugs, when used alone, is confronted with the emergence of resistant mutants. This led to the introduction of combination therapy of several anti-HIV agents usually having a different activity profile. In particular the introduction of "HAART" (Highly Active Anti-Retro viral Therapy) resulted in a remarkable improvement in anti-HIV therapy, leading to a large reduction in HIV-associated mortality. Even HAART may face the emergence of resistance, often due to non-adherence and non-persistence with antiretroviral therapy. In these cases HAART can be made effective again by replacing one of its components by one of another class. If applied correctly, treatment with HAART combinations can suppress the virus for many years, up to decades, to a level where it no longer can cause the outbreak of AIDS.

Combinations of anti-retrovirals create multiple obstacles to HIV replication to keep the number of offspring low and reduce the possibility of a superior mutation. If a mutation that conveys resistance to one of the drugs being taken arises, the other drugs continue to suppress reproduction of that mutation. Combination therapies greatly increase the ease with which they can be taken, which in turn increases the consistency with which medication is taken and thus their effectiveness over the long-term. Because of the complexity of selecting and following a regimen and the potential for side effects there lies an importance of taking medications regularly to prevent viral resistance.

The complex dosing regimens of HAART or other dosing regimens can be simplified by the application of combination dosage forms comprising two or more anti-HIV components. These could take the form of fixed dose combinations, e.g. compositions comprising predetermined doses of two or more anti-HIV agents. Most HIV inhibitors however need to be administered at relatively high doses so that often two or more doses need to be administered in order to reach the required therapeutic efficacy.

Currently available antiretroviral drugs for the treatment of HIV include nucleoside reverse transcriptase inhibitors (NRTI) or approved single pill combinations: Zidovudine or AZT (Retrovir®), didanosine or DDI (Videx®), stavudine or D4T (Zenith®), lamivudine or 3TC (Epivir®), zalcitabine or DDC (Hivid®), abacavir sulphate (Ziagen®), tenofovir disoproxil fumarate salt (Viread®), emtricitabine (Emtriva®), Combivir® (contains 3TC and AZT), Trizivir® (contains abacavir, 3TC and AZT); non-nucleoside reverse transcriptase inhibitors (NNRTI): nevirapine (Viramune®), delavirdine (Rescriptor®) and efavirenz (Sustiva®), peptidomimetic protease inhibitors or approved formulations: saquinavir (Invirase®, Fortovase®), indinavir (Crixivan®), ritonavir (Norvir®), nelfinavir (Viracept®), amprenavir (Agenerase®), atazanavir (Reyataz®), fosamprenavir (Lexiva®), Kaletra® (contains lopinavir and ritonavir), one fusion inhibitor enfuvirtide (T-20, Fuzeon®), Truvada® (contains Tenofovir disoproxil fumarate and Emtricitabine) and Atripla® (contains fixed-dose triple combination of tenofovir disoproxil fumarate, emtricitabine and efavirenz).

The current strategy recommended for the treatment of HIV infection is Highly Active Antiretroviral Therapy (HAART). HAART normally consists of a combination of two or more antiretroviral drugs (ARV) taken together in a single dosage form. Accordingly, inventors of the present invention have developed combination compositions having three antiretroviral drugs (ARV) taken together in a single dosage form with improved patient compliance.

Darunavir (TMC114) is a protease inhibitor approved in US and other countries, available under the trade name Prezista® in the form of darunavir ethanolate. It is chemically described as [(1S,2R)-3-[[(4-aminophenyl)sulfonyl](2-methylpropyl)amino]-2-hydroxy-1(phenylmethyl)propyl]-carbamic acid (3R,3aS,6aR)-hexahydrofuro[2,3-b]furan-3-yl ester monoethanolate.

Darunavir ethanolate is commercially available in US as 75 mg, 150 mg, 300 mg, 400 mg, 600 mg & 800 mg equivalent to base tablets and as equivalent to 100 mg base/ml oral suspension.

U.S. Pat. Nos. 5,843,946 & 7,700,645 discloses darunavir substance and its solvates including ethanolate.

PCT Publication No. 2009/013356 discloses darunavir tablet composition comprising 600 mg of darunavir as an active ingredient having a total weight of 1250 mg prepared by direct compression.

Dolutegravir sodium (DTG, GSK1349572) is an integrase inhibitor for the treatment of HIV infection. It is chemically described as (4R,12aS)-9-{[(2,4-difluorophenyl) methyl] carbamoyl}-4-methyl-6,8-dioxo-3,4,6,8,12,12a-hexahydro-2H-pyrido[1',2':4,5]pyrazino [2,1-b][1,3]oxazin-7-olate sodium. It commercially available in US as 10 mg, 25 mg and 50 mg equivalent to base tablets under the brand name TIVICAY®.

U.S. Pat. No. 8,129,385 discloses dolutegravir substance.

Ritonavir is protease inhibitor for the treatment of HIV infection. It is chemically described as 10-Hydroxy-2-methyl-5-(1-methylethyl)-1-[2-(1-methylethyl)-4-thiazolyl]-3,6-dioxo-8,11-bis(phenylmethyl)-2,4,7,12-tetraazatridecan-13-oic acid, 5-thiazolylmethyl ester, [5S-(5R*,8R*,10R*,11R*)].

Ritonavir is marketed under the trade name Norvir® in the United States in the form of tablets, oral solution and capsules. It is commercially available in US as 100 mg tablets and as equivalent to 80 mg base/ml oral solution.

U.S. Pat. No. 5,541,206 discloses ritonavir substance.

Inventors of the present invention have developed a solid dosage form comprising novel combination of darunavir, dolutegravir and ritonavir (combination therapy) used for treating HIV, helps in preventing drug resistance. Also provides the dosage form with acceptable size, easy to swallow and reduced dosing frequency. Hence, present dosage form is beneficial in terms of pill burden and increase the patient compliance.

SUMMARY OF THE INVENTION

The present invention relates to pharmaceutical tablet composition. In particular, the present invention relates to solid oral composition, comprising combination of anti-retro virals particularly, darunavir, dolutegravir and ritonavir and process of manufacturing the same.

The object of the present invention is to provide a pharmaceutical antiretroviral composition comprising darunavir, dolutegravir and ritonavir, in the form of a single unit dosage form.

One embodiment of the present invention relates to bilayered tablet composition comprising darunavir, dolutegravir and ritonavir and one or more pharmaceutically acceptable excipients.

Another embodiment of the present invention relates to a tablet composition comprising (i) Darunavir or a pharmaceutically acceptable solvate thereof, (ii) dolutegravir or a pharmaceutically acceptable salt thereof and (iii) ritonavir and one or more pharmaceutically acceptable excipients.

Another embodiment of the present invention relates to a tablet composition comprising darunavir or a pharmaceutically acceptable solvate thereof and dolutegravir or a pharmaceutically acceptable salt thereof with one or more pharmaceutically acceptable excipients.

Another embodiment of the present invention relates to a bilayered tablet composition comprising: a) Darunavir or its pharmaceutically acceptable solvate thereof, b) Dolutegravir or its pharmaceutically acceptable salt thereof, c) Ritonavir, d) one or more pharmaceutically acceptable excipients; wherein weight of the first part ranges from 1050 mg-1250 mg, weight of the second part ranges from 600 mg-750 mg, wherein total weight of the tablet ranges from 1650 mg-2000 mg.

One another embodiment of the present invention relates to a tablet composition comprising darunavir, dolutegravir, ritonavir and one or more pharmaceutically acceptable excipients; wherein weight of the first part ranges from 1050 mg-1250 mg, characterized by bulk density of 0.45-0.7 gm/cm³ and weight of the second part ranges from 600 mg-750 mg, characterized by bulk density of 0.5-0.7 gm/cm³.

One other embodiment of the present invention relates to a tablet composition comprising first part and second part, wherein first part comprising combination of darunavir and dolutegravir and second part comprising ritonavir, wherein weight of the first part ranges from 1050 mg-1250 mg, characterized by bulk density of 0.45-0.7 gm/cm³ and weight of the second part ranges from 600 mg-750 mg, characterized by bulk density of 0.5-0.7 gm/cm³, wherein total weight of the tablet ranges from 1650 mg-2000 mg.

By "total weight of the tablet" is meant the weight of a tablet including the first and the second parts without coating.

One other embodiment of the present invention relates to a tablet composition comprising first part and second part, wherein first part and second part are in the form of powder or granules.

One other embodiment of the present invention relates to a caplet dosage form comprising darunavir, dolutegravir, ritonavir and one or more excipients, wherein caplet is having a length of 15 to 22 mm, width of 7 to 11 mm and thickness 8.0 to 9.5 mm.

One other embodiment of the present invention relates to a caplet dosage form comprising 800 mg of darunavir, 50 mg of dolutegravir, 100 mg of ritonavir and one or more excipients, wherein caplet is having 8.0 to 9.5 mm thickness.

One other embodiment of the present invention relates to a caplet dosage form comprising darunavir, dolutegravir, ritonavir and one or more excipients, wherein caplet is having a length of 18 to 22 mm, width of 8 to 11 mm and thickness 8.0 to 9.5 mm.

One other embodiment of the present invention relates to tablet composition comprising darunavir, dolutegravir and ritonavir and one or more pharmaceutically acceptable excipients for once daily administration.

In yet another embodiment, the present invention is related to pharmaceutical unit dosage form comprising a) 300 mg to 800 mg of darunavir, b) 50 mg of dolutegravir, c) 100 mg of ritonavir and d) one or more pharmaceutically acceptable excipients.

In further embodiment, the present invention relates to the method of treating HIV or AIDS comprising administering a therapeutically effective amount of the tablet composition of the present invention.

DETAILED DESCRIPTION OF THE INVENTION

The present invention relates to tablet composition comprising combination of anti-retro virals particularly, darunavir, dolutegravir and ritonavir and process of manufacturing the same.

One embodiment of the present invention relates to pharmaceutical tablet comprising darunavir, dolutegravir and ritonavir with one or more pharmaceutically acceptable excipients thereof.

The term "active agent" as used herein according to the present invention refers to "darunavir", "dolutegravir" and "ritonavir".

The term "darunavir" as used herein according to the present invention includes darunavir in the form of free base or a pharmaceutically acceptable solvates or salts or its hydrates, preferably darunavir ethanolate.

The term "dolutegravir" as used herein according to the present invention includes dolutegravir in the form of free base or a pharmaceutically acceptable salt or solvate thereof. Preferably, dolutegravir sodium.

The term "bulk density" as used herein according to the present invention is bulk density of a powder or granules and is the ratio of the mass of an untapped powder or granules sample and its volume including the contribution of the interparticulate void volume. Hence, the bulk density depends on both the density of powder or granules and the spatial arrangement of particles in the powder or granular bed. The bulk density is expressed in grams per milliliter (g/ml) although the international unit is kilogram per cubic metre (1 g/ml=1000 kg/m$^3$) because the measurements are made using cylinders. It may also be expressed in grams per cubic centimeter (g/cm$^3$).

The bulk density of a powder is determined by measuring the volume of a known mass of powder sample, that may have been passed through a sieve, into a graduated cylinder (Method A), or by measuring the mass of a known volume of powder that has been passed through a volumeter into a cup (Method B) or a measuring vessel (Method C).

Important physicochemical characteristics of powders are the density properties such as bulk and tapped density, weight variation and flow properties such as angle of repose. Bulk density is the undisturbed packing density of that substance and tapped density relates to the packing density after tapping a bed of substance until no change in the packing density is seen. Bulk density and tapped density, can be determined using compendial bulk density apparatus, such as the method given in Test 616 "Bulk Density and Tapped Density," United States Pharmacopeia 39, United States Pharmacopeial Convention, Inc., Rockville, Md., 2005 ("USP"). The bulk density is measured in a graduated cylinder according to the European Pharmacopeia.

Bulk density determination: For the determination of bulk density of granules, the method suggested by Butler, Ransey and Martin was used. A sample of about 500 cc of the sized granules carefully introduced into a 100 cc graduated cylinder. The cylinder was then dropped onto a hard wood surface (table top) three times from a height of about one inch approximately two second intervals. Bulk density was then determined by dividing the weight of the sample of granules in grams by the final volume in cc. of the sample contained in the cylinder.

As used in this specification and the appended claims, the singular forms "a", "an", and "the" include plural references unless the context clearly dictates otherwise. Thus for example, reference to "a method" includes one or more methods, and/or steps of the type described herein and/or which will become apparent to those persons skilled in the art upon reading this disclosure so forth.

The term "excipient" means a pharmacologically inactive component such as a diluent, a binder, a disintegrant, a glidant, a lubricant, etc of a pharmaceutical product. The excipients that are useful in preparing a pharmaceutical composition are generally safe, non-toxic and are acceptable for human pharmaceutical use. Reference to an excipient includes both one and more than one such excipients.

The term "solid dosage form" or "dosage form" or "unitary composition" or "unit dosage form" or "composition" or "formulation" or "tablet" or "caplet" as used herein refers to a solid dosage form suitable for oral administration, such as tablets including layered tablets, capsules, mini-tablets, spheroids, pellets, granules, pills and the like meant for oral administration.

The term "part" also used herein synonymously as "compartment" or "layer".

By the term "core" is meant the granulate phase including the active agents and excipients.

By "total weight of the tablet" is meant the weight of a tablet including the first and the second parts without coating.

The term "immediate release" as used herein refers to a dosage form that disintegrates and dissolves rapidly to release the actives.

Suitably, the pharmaceutical antiretroviral composition according to the present invention is presented in the solid dosage form suitable for oral administration. However, other dosage forms, such as liquid dosage forms and the like, may be envisaged under the ambit of the present invention.

Unit dosage form, according to the present invention, are preferably in the form of a tablet (disintegrating tablet, dissolving tablet, dispersible tablet, mouth dissolving tablets, tablet for oral suspension, immediate release tablets, extended release tablet, immediate and extended release tablets, matrix tablets), mini-tablet, granules, sprinkles (filled with powders, powders for reconstitution; beads; pellets; mini-tablets; film coated tablets; film coated tablets MUPS (multiple unit pellet system); orally disintegrating MUPS; pills; micro-pellets; small tablet units; MUPS; granules; effervescent granules; microspheres) or capsule (filled with powders, powder for reconstitution; beads; pellets; mini-tablets; film coated tablets; film coated tablets MUPS; orally disintegrating MUPS; pills; micro-pellets; small tablet units; MUPS; disintegrating tablets; dispersible tablets; granules; effervescent granules; microspheres), liquids such as suspension, emulsion, solution, syrup, elixir however, other dosage forms may also fall within the scope of this invention.

Preferably, the pharmaceutical antiretroviral composition, according to the present invention, is in the form of solid unit dosage forms including tablets and capsules, preferably in the form of immediate release tablets.

Another embodiment of the present invention relates to a tablet composition comprising darunavir or a pharmaceutically acceptable solvate thereof and dolutegravir or a pharmaceutically acceptable salt thereof with one or more pharmaceutically acceptable excipients.

The composition of the present invention includes a high dose of darunavir, dolutegravir, ritonavir and excipients having a specific bulk density. The composition is dimensioned to form a caplet. The caplets may be prepared such that the length should not exceed 22 mm, width should not exceed 11 mm and thickness should not exceed 9 mm.

The said caplet is having different shapes like oblong shape, oval shape, modified capsule shape etc.

One embodiment of the present invention relates to pharmaceutical tablet composition comprising darunavir, dolutegravir and ritonavir with one or more pharmaceutically acceptable excipients in the form of tablet, wherein, darunavir and dolutegravir is present in first part and ritonavir is present in the second part.

One other embodiment of the present invention relates to pharmaceutical tablet composition comprising darunavir, dolutegravir and ritonavir with one or more pharmaceutically acceptable excipients in the form of bilayered tablet, wherein, darunavir and dolutegravir is present in first part and ritonavir is present in the second part, wherein weight of the first part ranges from 1050 mg-1250 mg, characterized by bulk density of 0.45-0.7 gm/cm$^3$ and weight of the second part ranges from 600 mg-750 mg, characterized by bulk density of 0.5-0.7 gm/cm$^3$, wherein total weight of the tablet ranges from 1650 mg-2000 mg.

One other embodiment of the present invention relates to a tablet composition comprising first part and second part, wherein first part and second part are in the form of powder or granules.

One other embodiment of the present invention relates to a caplet dosage form comprising darunavir, dolutegravir, ritonavir and one or more excipients, wherein caplet having a length of 15 to 22 mm, width of 7 to 11 mm and thickness of 8.0 to 9.5 mm.

One other embodiment of the present invention relates to a caplet dosage form comprising darunavir, dolutegravir, ritonavir and one or more excipients, wherein caplet is having a length of 18 to 22 mm, width of 8 to 11 mm and thickness 8.0 to 9.5 mm.

One other embodiment of the present invention relates to a caplet comprising 800 mg of darunavir, 50 mg of dolutegravir and 100 mg of ritonavir with one or more pharmaceutically acceptable excipients, wherein caplet is having 8.0 to 9.5 mm in thickness.

Further embodiment of the present invention relates to pharmaceutical tablet composition comprising a) 300 mg to 800 mg of darunavir, b) 50 mg of dolutegravir, c) 100 mg of ritonavir and d) one or more pharmaceutically acceptable excipients.

One or more pharmaceutically acceptable excipients of the present invention include diluents, binders, disintegrants, glidants, lubricants and the like.

Diluents include but are not limited to microcrystalline cellulose, powdered cellulose, lactose anhydrous, lactose monohydrate, dibasic calcium phosphate, tribasic calcium phosphate, starch, pregelatinized starch, calcium carbonate, calcium sulfate, magnesium carbonate, magnesium oxide, sucrose, dextrates, dextrin, dextrose, maltodextrin, mannitol, xylitol and sorbitol, and the like and combinations thereof.

Binders include but are not limited to hydroxypropyl cellulose, hydroxypropyl methylcellulose, polyvinyl pyrrolidone, pregelatinized starch, powdered acacia, gelatin, guar gum, carbomers and the like and combinations thereof.

Disintegrants include but are not limited to croscarmellose sodium, sodium starch glycolate, crospovidone, polacrillin potassium, carboxymethyl cellulose calcium, starches such as corn starch, potato starch, pregelatinized starch and modified starches, clays, bentonite and the like or combinations thereof.

Glidants include but are not limited to colloidal silicon dioxide, other forms of silicon dioxide, such as aggregated silicates and hydrated silica, magnesium silicate, magnesium trisilicate, talc, and the like and combinations thereof.

Lubricants include but are not limited to talc, magnesium stearate, calcium stearate, zinc stearate, stearic acid, palmitic acid, sodium stearyl fumarate, carnauba wax, hydrogenated vegetable oils, mineral oil, polyethylene glycols, and the like and combinations thereof.

The pharmaceutical antiretroviral composition, according to the present invention, may be prepared through various processes known in the art which includes, but are not limited to direct compression, wet granulation, dry granulation, melt granulation, melt extrusion, spray drying, solution evaporation or combinations thereof.

Pharmaceutical compositions of the present invention are prepared by either granulation techniques or direct compression. Preferably, first layer is prepared by granulation process and second layer is prepared by melt extrusion process.

Another aspect of the present invention relates to the tablet composition comprising darunavir, dolutegravir and ritonavir and one or more pharmaceutically acceptable excipients for once daily administration.

Even though such once-daily therapies represent a significant advantage, it would be highly desirable to faster the ease of administration, reduce dosing frequency and help ensure patient compliance with such once daily therapies in the form of a tablet dosage form.

In yet another embodiment, the present invention relates to method of treating HIV or AIDS comprising administering a therapeutically effective amount of the composition of the present invention.

Certain specific aspects and embodiments of this invention are described in further detail by the examples below, which are provided only for the purpose of illustration and are not intended to limit the scope of the invention in any manner.

EXAMPLES

Example 1: Darunavir, Dolutegravir and Ritonavir Bilayered Tablet

| Ingredients | mg/tab |
|---|---|
| DARUNAVIR + DOLUTEGRAVIR LAYER | |
| Darunavir Ethanolate | 867.296 |
| Dolutegravir sodium | 52.622 |
| Mannitol | 54.982 |
| Sodium starch glycolate | 32.000 |
| Povidone | 42.500 |
| Purified Water | Qs |
| Lubrication | |
| Sodium stearyl fumarate | 10.600 |
| Layer Weight | 1060.000 |
| RITONAVIR LAYER | |
| Ritonavir | 100.000 |
| Copovidone | 350.000 |
| Colloidal silicon dioxide | 1.000 |
| Sorbitan monolaurate | 45.000 |
| Prelubrication | |
| Dibasic calcium phosphate anhydrous | 15.500 |
| Colloidal silicon dioxide | 1.000 |
| Lubrication | |
| Sodium stearyl fumarate | 5.500 |
| Layer Weight | 518.000 |
| Core Tablet weight | 1578.000 |
| Film coated tablet weight | 1625.340 |

Brief Manufacturing Process:

Preparation of Darunavir+Dolutegravir Layer:

a) Sifting darunavir, dolutegravir, mannitol and sodium starch glycolate and then loading into rapid mixer granulator and mixing for 10 minutes, b) dissolving povidone in purified water and adding to the blend of step a) and kneading the wet mass, followed by drying, sifting to get the desired size granules, c) sifting sodium stearyl fumarate, d) mixing granules of step b) with sodium stearyl fumarate of step c) in blender;

Preparation of Ritonavir Layer:

a) Sifting ritonavir, copovidone and colloidal silicon dioxide and b) adding sorbitan monolaurate to step a) and passing the material through hot melt extruder and collect the extrudes, c) sifting dibasic calcium phosphate anhydrous and colloidal silicon dioxide and adding the material to step b) and blending for 10 minutes, d) sifting sodium stearyl fumarate and adding to material of step c) and blending for 5 minutes;

Compression of Bilayered Tablets:

Compressing the above blends of darunavir+dolutegravir in one layer and ritonavir in another layer into bilayered tablets, followed by film-coating.

Bulk Density:

| Bulk density | Darunavir + Dolutegravir layer: 0.51 gm/cm³ Ritonavir layer: 0.53 gm/cm³ |
|---|---|

Thickness: 7.5±0.1 (of tablet)
Dissolution Profile:

| Time in minutes | % of drug released | | |
|---|---|---|---|
| | Darunavir | Dolutegravir | Ritonavir |
| 30 | 66 | 83 | 26 |
| 60 | 89 | 92 | 39 |
| 90 | 94 | 95 | 45 |
| 120 | 96 | 95 | 48 |

Example 2: Darunavir, Dolutegravir and Ritonavir Bilayered Tablet

| Ingredients | mg/tab |
|---|---|
| DARUNAVIR + DOLUTEGRAVIR LAYER | |
| Darunavir Ethanolate | 867.296 |
| Dolutegravir sodium | 52.622 |
| Mannitol | 54.982 |
| Sodium starch glycolate | 32.000 |
| Povidone | 42.500 |
| Purified Water | Qs |
| Lubrication | |
| Sodium stearyl fumarate | 10.600 |
| Layer Weight | 1060.000 |
| RITONAVIR LAYER | |
| Ritonavir | 100.000 |
| Copovidone | 458.810 |
| Colloidal silicon dioxide | 0.540 |
| Sorbitan monolaurate | 42.000 |
| Prelubrication | |
| Dibasic calcium phosphate anhydrous | 74.750 |
| Colloidal silicon dioxide | 0.750 |
| Lubrication | |
| Sodium stearyl fumarate | 6.150 |
| Layer Weight | 683.000 |
| Core Tablet weight | 1743.000 |
| Film coated tablet weight | 1795.290 |

Brief Manufacturing Process:
Preparation of Darunavir+Dolutegravir Layer:
a) Sifting darunavir, dolutegravir, mannitol and sodium starch glycolate and then loading into rapid mixer granulator and mixing for 10 minutes,
b) dissolving povidone in purified water and adding to the blend of step a) and kneading the wet mass, followed by drying, sifting to get the desired size granules,
c) sifting sodium stearyl fumarate,
d) mixing granules of step b) with sodium stearyl fumarate of step c) in blender
Preparation of Ritonavir Layer:
a) Sifting ritonavir, copovidone and colloidal silicon dioxide and
b) adding sorbitan monolaurate to step a) and passing the material through hot melt extruder and collect the extrudes,
c) sifting dibasic calcium phosphate anhydrous and colloidal silicon dioxide and adding the material to step b) and blending for 10 minutes,
d) sifting sodium stearyl fumarate and adding to material of step c) and blending for 5 minutes;
Compression of Bilayered Tablets:
Compress the above blends of darunavir+dolutegravir in one layer and ritonavir in another layer into bilayered tablets, followed by film-coating.
Bulk Density:

| Bulk density | Darunavir + Dolutegravir layer: 0.52 gm/cm³ Ritonavir layer: 0.60 gm/cm³ |
|---|---|

Thickness: 9.2±0.1 (of tablet)
Dissolution Profile:

| Time in minutes | % of drug released | | |
|---|---|---|---|
| | Darunavir | Dolutegravir | Ritonavir |
| 30 | 63 | 82 | 59 |
| 60 | 91 | 89 | 90 |
| 90 | 97 | 89 | 96 |
| 120 | 99 | 89 | 98 |

Example 3: Darunavir, Dolutegravir and Ritonavir Bilayered Tablet

| Ingredients | mg/tab |
|---|---|
| DARUNAVIR + DOLUTEGRAVIR LAYER | |
| Darunavir Ethanolate | 867.296 |
| Dolutegravir sodium | 52.622 |
| Microcrystalline cellulose | 54.982 |
| Sodium starch glycolate | 32.000 |
| Hydroxypropyl cellulose | 42.500 |
| Purified Water | Qs |
| Lubrication | |
| Sodium stearyl fumarate | 10.600 |
| Layer Weight | 1060.000 |
| RITONAVIR LAYER | |
| Ritonavir | 100.000 |
| Copovidone | 430.000 |
| Colloidal silicon dioxide | 1.000 |
| Sorbitan monolaurate | 36.000 |
| Prelubrication | |
| Dibasic calcium phosphate anhydrous | 40.000 |
| Colloidal silicon dioxide | 3.000 |
| Lubrication | |
| Sodium stearyl fumarate | 5.500 |
| Layer Weight | 615.500 |
| Core Tab weight | 1675.500 |
| Film Coated tablet weight | 1725.765 |

Brief Manufacturing Process:
Preparation of Darunavir+Dolutegravir Layer:
a) Sifting darunavir, dolutegravir, microcrystalline cellulose, sodium starch glycolate and then loading into rapid mixer granulator and mixing for 10 minutes,
b) dissolving hydroxypropyl cellulose in purified water and adding to the blend of step a) and kneading the wet mass, followed by drying, sifting to get the desired size granules, c) sifting sodium stearyl fumarate,
d) mixing granules of step b) with sodium stearyl fumarate of step c) in blender Preparation of Ritonavir Layer:
a) Sifting ritonavir, copovidone and colloidal silicon dioxide and
b) adding sorbitan monolaurate to step a) and passing the material through hot melt extruder and collect the extrudes,
c) sifting dibasic calcium phosphate anhydrous and colloidal silicon dioxide and adding the material to step b) and blending for 10 minutes,
d) sifting sodium stearyl fumarate and adding to material of step c) and blending for 5 minutes;

Compression of Bilayered Tablets:
Compress the above blends of darunavir+dolutegravir in one layer and ritonavir in another layer into bilayered tablets, followed by film-coating.

Bulk Density:

| Bulk density | Darunavir + Dolutegravir layer: 0.50 gm/cm$^3$<br>Ritonavir layer: 0.56 gm/cm$^3$ |
|---|---|

Thickness: 8.2±0.1 (of tablet)

Example 4

Darunavir, Dolutegravir and Ritonavir Bilayered Tablet:

| Ingredients | mg/tab |
|---|---|
| DARUNAVIR + DOLUTEGRAVIR LAYER | |
| Darunavir Ethanolate | 867.296 |
| Dolutegravir sodium | 52.622 |
| Mannitol | 55.082 |
| Pregelatinized starch | 77.000 |
| Povidone | 43.000 |
| Purified Water | Qs |
| Lubrication | |
| Sodium stearyl fumarate | 11.000 |
| Layer Weight | 1106.000 |
| RITONAVIR LAYER | |
| Ritonavir | 100.000 |
| Copovidone | 400.100 |
| Colloidal silicon dioxide | 1.000 |
| Sorbitan monolaurate | 42.000 |
| Pre-lubrication | |
| Dibasic calcium phosphate anhydrous | 50.000 |
| Colloidal silicon dioxide | 0.700 |
| Lubrication | |
| Sodium stearyl fumarate | 6.150 |
| Layer Weight | 600.000 |
| Core Tab weight | 1706.000 |
| Film Coated tablet weight | 1757.180 |

Brief Manufacturing Process:
Preparation of Darunavir+Dolutegravir Layer:
a) Sifting darunavir, dolutegravir, mannitol and pregelatinized starch and then loading into rapid mixer granulator and mix for 10 minutes,
b) dissolving povidone in purified water and adding to the blend of step a) kneading the wet mass, followed by drying, sifting to get the desired size granules,
c) sifting sodium stearyl fumarate,
d) mixing granules of step b) with sodium stearyl fumarate of step c) into blender and compressing into tablets;

Preparation of Ritonavir Layer:
a) Sifting ritonavir, copovidone and colloidal silicon dioxide through mesh,
b) adding sorbitan monolaurate to step a) and pass the material through hot melt extruder and collect the extrudes,
c) sifting dibasic calcium phosphate anhydrous and colloidal silicon dioxide together through mesh, add the material to step b) blending for 10 minutes,
d) adding sodium stearyl fumarate to material of step c) and blend for 5 minutes;

Compression of Bilayered Tablets:
Compress the above blends of darunavir+dolutegravir in one layer and ritonavir in another layer into bilayered tablets, followed by film-coating.

Bulk Density:

| Bulk density | Darunavir + Dolutegravir layer: 0.53 gm/cm$^3$<br>Ritonavir layer: 0.60 gm/cm$^3$ |
|---|---|

Thickness: 8.5±0.1 (of tablet)

Example 5: Darunavir, Dolutegravir and Ritonavir Bilayered Tablet

| Ingredients | mg/tab |
|---|---|
| DARUNAVIR + DOLUTEGRAVIR LAYER | |
| Darunavir Ethanolate | 867.296 |
| Dolutegravir sodium | 52.622 |
| Mannitol | 55.082 |
| Microcrystalline cellulose | 44.982 |
| Sodium starch glycolate | 57.000 |
| Povidone | 43.000 |
| Purified Water | Qs |
| Lubrication | |
| Sodium stearyl fumarate | 12.000 |
| Layer Weight | 1131.982 |
| RITONAVIR LAYER | |
| Ritonavir | 100.000 |
| Copovidone | 508.810 |
| Colloidal silicon dioxide | 1.000 |
| Sorbitan monolaurate | 52.000 |
| Prelubrication | |
| Dibasic calcium phosphate anhydrous | 94.750 |
| Colloidal silicon dioxide | 0.750 |
| Lubrication | |
| Sodium stearyl fumarate | 6.150 |
| Layer Weight | 763.460 |
| Core Tab weight | 1895.442 |
| Film Coated tablet weight | 1952.305 |

Brief Manufacturing Process:
Preparation of Darunavir+Dolutegravir Layer:
a) Sifting darunavir, dolutegravir, mannitol, microcrystalline cellulose and sodium starch glycolate and then load into rapid mixer granulator and mix for 10 minutes,
b) dissolving povidone in purified water and add to the blend of step a) knead the wet mass, followed by drying, sifting to get the desired size granules, c) sifting sodium stearyl fumarate,
d) mixing granules of step b) with sodium stearyl fumarate of step c) into blender and compressing into tablets;

Preparation of Ritonavir Layer:
a) Sifting ritonavir, copovidone and colloidal silicon dioxide through mesh,
b) adding sorbitan monolaurate to step a) and pass the material through hot melt extruder and collect the extrudes,
c) sifting dibasic calcium phosphate anhydrous and colloidal silicon dioxide together through mesh, add the material to step b) blending for 10 minutes,
d) adding sodium stearyl fumarate to material of step c) and blend for 5 minutes;

Compression of Bilayered Tablets:
Compression of above ritonavir extrudes with darunavir+dolutegravir layered tablets to obtain bilayered tablets and film-coating the obtained bilayered tablets.

Bulk Density:

| Bulk density | Darunavir + Dolutegravir layer: 0.54 gm/cm$^3$<br>Ritonavir layer: 0.60 gm/cm$^3$ |
|---|---|

Thickness: 10.0±0.1 (of tablet), which is not suitable for swallowing thereby, invites patient compliance problems.

Test Results:
Physical Parameters:

| Example | First layer wt. | Second layer wt. | Total wt. of core tablet | Thickness | Bulk density | |
|---|---|---|---|---|---|---|
| | | | | | Darunavir + Dolutegravir Layer | Ritonavir Layer |
| 1 | 1060 | 518 | 1578 | 7.5 ± 0.1 mm | 0.51 | 0.53 |
| 2 | 1060 | 683 | 1743 | 9.2 ± 0.1 mm | 0.52 | 0.62 |
| 3 | 1060 | 615.500 | 1675.5 | 8.2 ± 0.1 mm | 0.50 | 0.56 |
| 4 | 1106 | 600 | 1706 | 8.5 ± 0.1 mm | 0.53 | 0.69 |
| 5 | 1131.982 | 763.460 | 1895.442 | 10.0 ± 0.1 mm | 0.54 | 0.61 |

Above results indicate that thickness of 8.0±0.1 mm to 9.2±0.1 mm shows improved dissolution profile over tablets having thickness of less than 8.0 mm.

Further, it was observed that tablets having thickness of 10.0±0.1 mm and above will pose problems of patient compliance, feeling difficulty in swallowing.

Dissolution Profile:

TABLE A (Test results):

| Time in minutes | Example 1 | | | Example 2 | | |
|---|---|---|---|---|---|---|
| | Darunavir | Dolutegravir | Ritonavir | Darunavir | Dolutegravir | Ritonavir |
| 30 | 66 | 83 | 26 | 63 | 82 | 59 |
| 60 | 89 | 92 | 39 | 91 | 89 | 90 |
| 90 | 94 | 95 | 45 | 97 | 89 | 96 |
| 120 | 96 | 95 | 48 | 99 | 89 | 98 |

TABLE B (Innovator dissolution profiles for plain marketed tablets):

| | % of drug released | | |
|---|---|---|---|
| Time in minutes | Darunavir (Prezista ®) | Dolutegravir (Tivicay ®) | Ritonavir (Norvir ®) |
| 30 | 94 | 97 | 42 |
| 60 | 98 | 97 | 75 |
| 90 | 99 | 95 | 90 |
| 120 | 100 | 94 | 96 |

From the results shown in Table A, it was observed that tablets (Example 2) with specific physical parameters of the present invention could produce better dissolution without any delay as compared to example 1.

Drug release for the tablets of the present invention (Example 2) for three active agents found to be comparable with Innovator product drug release.

We claim:
1. A bilayer tablet composition comprising
   (a) a first layer comprising a combination of 300 to 800 mg of darunavir base equivalent, 50 mg of dolutegravir base equivalent, and first layer pharmaceutically acceptable excipients, wherein a total weight of the first layer ranges from 1050 mg-1250 mg, and the first layer is characterized by a bulk density of 0.45-0.7 gm/cm$^3$, and
   (b) a second layer comprising 100 mg of ritonavir, and second layer pharmaceutically acceptable excipients, wherein a total weight of the second layer ranges from 600 mg-750 mg, and the second layer is characterized by bulk density of 0.5-0.7 gm/cm$^3$,
   wherein a total weight of the bilayer tablet ranges from 1650 mg-2000 mg.

2. The bilayer tablet composition of claim 1, wherein the first layer and second layer are in the form of granules.

3. The bilayer tablet composition of claim 1, wherein the darunavir is darunavir ethanolate, and the dolutegravir is dolutegravir sodium.

4. The bilayer tablet of claim 1, in the form of a bilayer caplet comprising 800 mg of darunavir base equivalent, and 50 mg of dolutegravir base wherein the caplet has an 8.0 to 9.5 mm thickness.

5. The bilayer tablet of claim 4, having a length of 15 to 22 mm and a width of 7 to 11 mm.

6. The bilayer tablet composition of claim 1, wherein the darunavir is present in an amount of 800 mg darunavir base equivalent, the dolutegravir is present in an amount of 50 mg dolutegravir base equivalent, and the ritonavir is present in an amount of 100 mg.

7. The bilayer tablet composition of claim 1, in the form of an immediate release bilayered tablet.

8. The bilayer tablet composition of claim 1, wherein the first layer is prepared by wet granulation, dry granulation or direct compression, and the second layer is prepared by hot melt extrusion.

9. A method of treating HIV comprising administering a therapeutically effective amount of the tablet composition as defined in claim 1.

* * * * *